(12) United States Patent
Vogt et al.

(10) Patent No.: US 11,885,073 B2
(45) Date of Patent: Jan. 30, 2024

(54) DURABLE AND DISPERSIBLE CREPED MUTLI-PLY TISSUE

(71) Applicant: Kimberly-Clark Worldwide, Inc., Neenah, WI (US)

(72) Inventors: Kevin Joseph Vogt, Neenah, WI (US); Mark William Sachs, Appleton, WI (US); Erin Ann McCormick, Neenah, WI (US); Devon Gaynelle Curley, Menasha, WI (US); Sara Jane Wille Stabelfeldt, Appleton, WI (US); Nathan John Vogel, Neenah, WI (US); Christopher Steven LeCount, Greenville, WI (US)

(*) Notice: Subject to any disclaimer, the term of this patent is extended or adjusted under 35 U.S.C. 154(b) by 0 days.

(21) Appl. No.: 18/136,389

(22) Filed: Apr. 19, 2023

(65) Prior Publication Data
US 2023/0272586 A1 Aug. 31, 2023

Related U.S. Application Data

(63) Continuation of application No. 17/749,318, filed on May 20, 2022, now Pat. No. 11,661,707, which is a (Continued)

(51) Int. Cl.
*D21H 27/40* (2006.01)
*A47K 10/16* (2006.01)
(Continued)

(52) U.S. Cl.
CPC ............ *D21H 27/40* (2013.01); *A47K 10/16* (2013.01); *B31F 1/12* (2013.01); *D21H 27/005* (2013.01);
(Continued)

(58) Field of Classification Search
CPC .... D21H 27/40; D21H 27/005; D21H 27/002; D21H 27/02; B31F 1/07; B31F 1/126;
(Continued)

(56) References Cited

U.S. PATENT DOCUMENTS

| 4,063,995 A | 12/1977 | Grossman |
| 4,886,579 A | 12/1989 | Clark et al. |

(Continued)

FOREIGN PATENT DOCUMENTS

| KR | 101794487 B1 | 11/2017 |
| WO | 2005113895 A1 | 12/2005 |

(Continued)

*Primary Examiner* — Jose A Fortuna
(74) *Attorney, Agent, or Firm* — Kimberly-Clark Worldwide, Inc.

(57) ABSTRACT

Disclosed are multi-ply tissue products comprising a non-crosslinked binder that are durable and dispersible. The products generally have a Slosh time less than 2 minutes, such as less than about 60 seconds, such as less than about 45 seconds. Surprisingly, the foregoing Slosh times are achieved despite the tissue products having relatively high cross-machine direction (CD) wet tensile strength, such as greater than about 100 g/3". Typically, increasing wet tensile strength, particularly wet CD tensile strength, negatively effects dispersability and increases Slosh time. Despite this trend, the present invention surprisingly provides a tissue product having a relatively high degree of wet strength and good dispersability.

20 Claims, 6 Drawing Sheets

Related U.S. Application Data continuation of application No. 17/417,184, filed as application No. PCT/US2020/025226 on Mar. 27, 2020, now Pat. No. 11,371,191.

(60) Provisional application No. 62/825,895, filed on Mar. 29, 2019.

(51) Int. Cl.
*D21H 27/00* (2006.01)
*B31F 1/12* (2006.01)
*B31F 1/07* (2006.01)

(52) U.S. Cl.
CPC ............... *B31F 1/07* (2013.01); *B31F 1/126* (2013.01); *B31F 2201/0715* (2013.01); *B31F 2201/0764* (2013.01)

(58) Field of Classification Search
CPC ...... B31F 2201/0715; B31F 2201/0764; B31F 1/14; B31F 2201/0761; B31F 1/12; A47K 10/16; A61K 8/0208; A61K 8/81
See application file for complete search history.

(56) References Cited

U.S. PATENT DOCUMENTS

| | | | |
|---|---|---|---|
| 8,282,776 B2 | 10/2012 | Smith et al. | |
| 9,121,137 B2 | 9/2015 | Viazmensky et al. | |
| 9,951,477 B2 | 4/2018 | Zwick et al. | |
| 10,132,041 B2 | 11/2018 | Hermans et al. | |
| 10,145,069 B2 | 12/2018 | Shannon et al. | |
| 10,337,148 B2 | 7/2019 | Rouse et al. | |
| 10,337,149 B2 | 7/2019 | Rouse et al. | |
| 10,385,516 B2 | 8/2019 | Zawadzki et al. | |
| 10,428,465 B2 | 10/2019 | Rouse et al. | |
| 10,487,452 B1 | 11/2019 | Qin et al. | |
| 10,550,522 B2 | 2/2020 | Shannon et al. | |
| 10,753,046 B2 | 8/2020 | Zawadzki et al. | |
| 10,947,673 B2 | 3/2021 | Rouse et al. | |
| 11,053,643 B2 | 7/2021 | Rouse et al. | |
| 11,371,191 B2 | 6/2022 | Vogt et al. | |
| 11,427,968 B2 | 8/2022 | Vogt et al. | |
| 11,661,707 B2 * | 5/2023 | Vogt .................... | D21H 27/002 162/111 |
| 11,773,538 B2 | 10/2023 | Vogt et al. | |
| 11,795,626 B2 * | 10/2023 | Vogt ....................... | D21H 27/30 |
| 2007/0144697 A1 | 6/2007 | Dyer et al. | |
| 2008/0073045 A1 | 3/2008 | Dyer et al. | |
| 2014/0050890 A1 | 2/2014 | Zwick et al. | |
| 2014/0178660 A1 | 6/2014 | Kim et al. | |
| 2016/0097163 A1 | 4/2016 | Rekoske et al. | |
| 2016/0145809 A1 | 5/2016 | Hermans et al. | |
| 2018/0016749 A1 | 1/2018 | Zawadzki et al. | |
| 2018/0142419 A1 | 5/2018 | Rouse et al. | |
| 2018/0142421 A1 | 5/2018 | Rouse et al. | |
| 2019/0309482 A1 | 10/2019 | Zawadzki et al. | |
| 2020/0032456 A1 | 1/2020 | Paulson et al. | |
| 2020/0035456 A1 | 1/2020 | Fan et al. | |
| 2020/0102705 A1 | 4/2020 | Rouse et al. | |
| 2020/0115853 A1 | 4/2020 | Shannon et al. | |
| 2021/0156093 A1 | 5/2021 | Rouse et al. | |
| 2021/0238806 A1 | 8/2021 | Tirimacco | |
| 2021/0277603 A1 | 9/2021 | Anderson et al. | |
| 2021/0285159 A1 | 9/2021 | Burazin et al. | |
| 2021/0292973 A1 | 9/2021 | Rouse et al. | |
| 2022/0042248 A1 | 2/2022 | Vogt et al. | |
| 2022/0090321 A1 | 3/2022 | Weisman et al. | |
| 2022/0178079 A1 * | 6/2022 | Tirimacco ............ | D21H 27/002 |
| 2022/0228322 A1 | 7/2022 | Vogt et al. | |
| 2022/0282428 A1 | 9/2022 | Vogt et al. | |
| 2022/0287924 A1 | 9/2022 | Monson et al. | |
| 2022/0332085 A1 | 10/2022 | Monson et al. | |
| 2022/0364310 A1 | 11/2022 | Vogt et al. | |

FOREIGN PATENT DOCUMENTS

| | | |
|---|---|---|
| WO | 2020205524 A1 | 10/2020 |
| WO | 2020247205 A1 | 12/2020 |
| WO | 2021194504 A1 | 9/2021 |
| WO | 2021194505 A1 | 9/2021 |

* cited by examiner

DURABLE AND DISPERSIBLE CREPED MUTLI-PLY TISSUE

RELATED APPLICATIONS

The present application is a continuation application and claims priority to U.S. patent application Ser. No. 17/749,318, filed May 20, 2022, now U.S. Pat. No. 11,661,707, which is a continuation application and claims priority to U.S. patent application Ser. No. 17/417,184, filed on Jun. 22, 2021, now U.S. Pat. No. 11,371,191, which is a national-phase entry, under 35 U.S.C. § 371, of PCT Patent Application No. PCT/US20/25226, filed on Mar. 27, 2020, which claims benefit of U.S. Provisional Application No. 62/825,895, filed on Mar. 29, 2019, all of which are incorporated herein by reference.

BACKGROUND

Single use tissue products, such as toilet paper, are designed to provide sufficient strength in-use, yet disintegrate in aqueous environments without clogging domestic waste disposal or septic systems. As such single use tissue products call for both dry and wet properties, such as good dry durability to withstand use and rapid breakup when wetted to ensure flushability.

Various technologies have been adapted to balance the dry and wet demands of single use tissue products. For example, U.S. Pat. No. 7,776,772 disclose water dispersible fibrous structure made from a blend of conventional wood pulp fibers and water soluble fibers such as polyvinyl alcohol. On the other hand, U.S. Pat. No. 7,838,725 discloses a multi-layered water dispersible fibrous structure where the layers, which have been mechanically weakened, are joined by a water sensitive binder such as polyvinyl alcohol or starch. While U.S. Pat. No. 8,088,252 discloses the use of an ion trigger binder to bind a fibrous structure during use yet provide for rapid disintegration upon dilution when disposed in the wastewater system.

There remains a need however, for tissue products that have both good dry durability to withstand use and rapid breakup when wetted to ensure flushability.

SUMMARY

The present invention provides creped tissue webs, and products produced therefrom, that are generally durable, flexible and highly dispersible. The inventive products generally comprise two or more tissue plies prepared by a creping and more preferably by a print creping process. In particularly preferred embodiments the plies are print creped using a non-crosslinked latex binder that is disposed on at least one of the outer surfaces of the tissue product to provide the product with improved durability. Surprisingly, however, the presence of the non-crosslinked latex binder does not negatively affect dispersability of the product. For example, in certain embodiments, tissue products prepared according to the present invention have a Slosh time less than 2 minutes, which is comparable to, or better than, commercially available multi-ply rolled bath tissue products.

Accordingly, in one embodiment the invention provides creped multi-ply tissue products comprising two or more creped tissue plies, wherein each of the creped tissue plies have a first and second outer surface and a non-crosslinked binder disposed on the first or the second surface. The multi-ply tissue products are high dispersible when wet, such as having a Slosh time less than 2 minutes, such as less than about 100 seconds, such as less than about 60 seconds, such as less than about 30 seconds, such as from about 10 seconds to 2 minutes, such as from about 10 seconds to about 60 seconds, such as from about 15 seconds to about 45 seconds.

In other embodiments the invention provides a highly dispersible and durable multi-ply tissue product comprising a non-crosslinked binder, the tissue product having relatively high cross-machine direction (CD) wet tensile strength, such as greater than about 100 g/3", such as greater than about 110 g/3", such as greater than about 120 g/3". Typically, increasing wet tensile strength, particularly wet CD tensile strength, negatively effects dispersability and increases Slosh time. Despite this trend, the present invention surprisingly provides a tissue product having a relatively high degree of wet strength and good dispersability, such as a Slosh time less than 2 minutes, such as less than about 100 seconds, such as less than about 60 seconds, such as less than about 30 seconds, such as from about 10 seconds to 2 minutes, such as from about 10 seconds to about 60 seconds, such as from about 15 seconds to about 45 seconds.

In another embodiment the present invention provides a durable and dispersible rolled tissue product comprising a creped multi-ply tissue product spirally wound about a core, the multi-ply tissue product having a geometric mean tensile strength (GMT) greater than about 700 g/3", a Durability Index greater than about 15.0 and a Slosh time less than about 45 seconds.

In yet other embodiments the present invention provides a creped, multi-ply tissue product comprising: (a) a first and a second tissue ply; (b) a creping composition consisting essentially of a non-crosslinked vinyl acetate-ethylene polymer and optionally an anti-blocking agent disposed on the first and the second tissue ply; (c) at least one softening composition selected from the group consisting of a poly-hydroxy compound having a molecular weight of at least about 1,000 g/mol, a diamidoamine quaternary compound, an ester quaternary compound, an alkoxy alkyl quaternary compound, a benzyl quaternary compound, an alkyl quaternary compound, an imidazolinium quaternary compounds, a polysiloxane, glycerin, and combinations thereof, disposed on the first or the second tissue ply; and (d) a plurality of embossments disposed on the first or the second tissue ply; wherein the product has a GMT less than 1,700 g/3" and a Slosh time less than about 2 minutes.

DEFINITIONS

Figure 1:
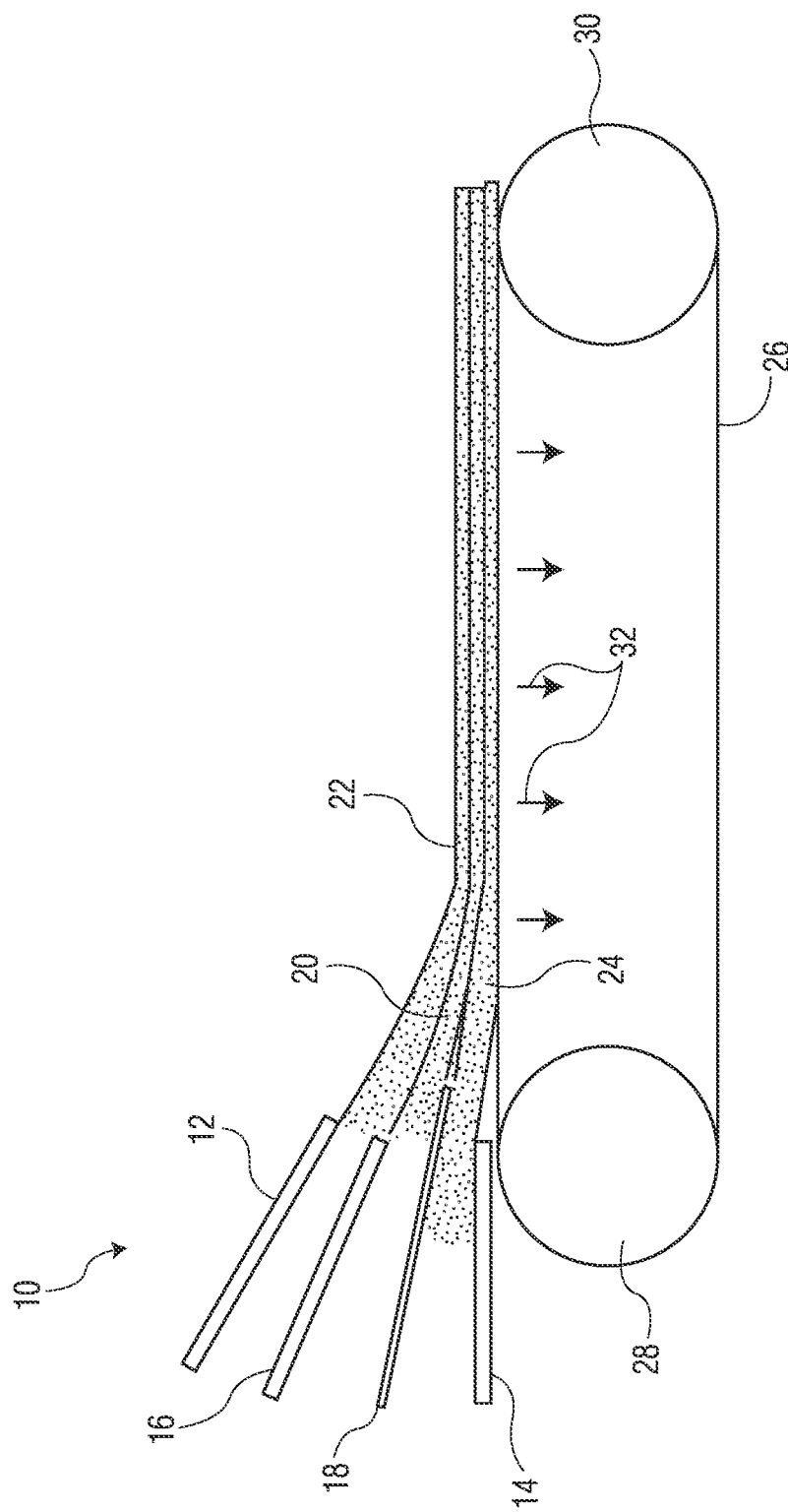
FIG. 1 illustrates one embodiment for forming a multi-layered tissue web according to the present invention.

As used herein the term "Basesheet" refers to a tissue web formed by any one of the papermaking processes described herein that has not been subjected to further processing, such as embossing, calendering, treatment with a binder or softening composition, perforating, plying, folding, or rolling into individual rolled products.

As used herein the term "Tissue Product" refers to products made from basesheets and includes, bath tissues, facial tissues, paper towels, industrial wipers, foodservice wipers, napkins, medical pads, and other similar products.

As used herein the term "Ply" refers to a discrete tissue web used to form a tissue product. Individual plies may be arranged in juxtaposition to each other. In a preferred embodiment, tissue products prepared according to the present invention comprise two creped tissue plies.

As used herein, the term "Layer" refers to a plurality of strata of fibers, chemical treatments, or the like, within a ply. A "Layered Tissue Web" generally refers to a tissue web formed from two or more layers of aqueous papermaking furnish. In certain instances, the aqueous papermaking furnish forming two or more of the layers comprise different fiber types.

As used herein the term "Basis Weight" generally refers to the conditioned weight per unit area of a tissue and is generally expressed as grams per square meter (gsm). Basis weight is measured as described in the Test Methods section below. While the basis weights of tissue products prepared according to the present invention may vary, in certain embodiments the products have a basis weight greater than about 20 gsm, such as greater than about 30 gsm, such as greater than about 40 gsm, such as from about 20 to about 80 gsm, such as from about 30 to about 60 gsm, such as from about 45 to about 55 gsm.

As used herein, the term "Caliper" refers to the thickness of a tissue product, web, sheet or ply, typically having units of microns (µm) and is measured as described in the Test Methods section below.

As used herein, the term "Sheet Bulk" refers to the quotient of the caliper (µm) divided by the bone dry basis weight (gsm). The resulting sheet bulk is expressed in cubic centimeters per gram (cc/g). Tissue products prepared according to the present invention may, in certain embodiments, have a sheet bulk greater than about 8.0 cc/g, more preferably greater than about 9.0 cc/g and still more preferably greater than about 10.0 cc/g, such as from about 8.0 to about 12.0 cc/g.

As used herein, the term "Slope" refers to the slope of the line resulting from plotting tensile versus stretch and is an output of the MTS TestWorks™ in the course of determining the tensile strength as described in the Test Methods section herein. Slope is reported in the units of grams (g) per unit of sample width (inches) and is measured as the gradient of the least-squares line fitted to the load-corrected strain points falling between a specimen-generated force of 70 to 157 grams (0.687 to 1.540 N) divided by the specimen width.

As used herein, the term "Geometric Mean Slope" (GM Slope) generally refers to the square root of the product of machine direction slope and cross-machine direction slope. While the GM Slope may vary amongst tissue products prepared according to the present disclosure, in certain embodiments, tissue products may have a GM Slope less than about 10.00 kg, more preferably less than about 9.00 kg and still more preferably less than about 8.50 kg, such as from about 6.00 to about 10.0 g, such as from about 6.00 to about 8.50 kg.

As used herein, the term "Geometric Mean Tensile" (GMT) refers to the square root of the product of the machine direction tensile strength and the cross-machine direction tensile strength of the web. The GMT of tissue products prepared according to the present invention may vary, however, in certain instances the GMT may be about 700 g/3" or greater, such as about 800 g/3" or greater, such as about 900 g/3" or greater, such as from about 700 about 1,700 g/3", such as from about 800 to about 1,500 g/3".

As used herein, the term "Stiffness Index" refers to the quotient of the geometric mean tensile slope, defined as the square root of the product of the MD and CD slopes (having units of kg), divided by the geometric mean tensile strength (having units of grams per three inches).

$$\text{Stiffness Index} = \frac{\sqrt{MD \text{ Tensile Slope (kg)} \times CD \text{ Tensile Slope (kg)}}}{GMT \text{ (g/3")}} \times 1{,}000$$

While the Stiffness Index of tissue products prepared according to the present disclosure may vary, in certain instances the Stiffness Index may be less than about 8.0, such as less than about 6.0, such as less than about 5.5, such as from about 4.0 to about 8.0, such as from about 4.0 to about 6.0.

As used herein, the term "Slosh" generally refers to the time needed to break-up a tissue sample into pieces less than 25×25 mm using the Slosh test as described in the Test Methods section below. Generally, Slosh has units of seconds or minutes. The Slosh test uses a bench-scaled apparatus to evaluate the breakup or dispersability of flushable consumer products as they travel through the wastewater collection system.

As used herein, the term "Wet/Dry Ratio" refers to the ratio of the wet cross-machine direction (CD) tensile strength to the dry CD tensile strength. Wet and dry CD tensile are measured as set forth in the Test Methods section below. The Wet/Dry Ratio of inventive tissue products may vary depending on several factors such as, for example, the creping composition and the amount of wet strength additive, however, in certain instances the inventive tissue products may have a Wet/Dry Ratio greater than about 0.10, such as greater than about 0.125, such as greater than about 0.150, such as from about 0.10 to about 0.20, such as from about 0.10 to about 0.15.

As used herein, the term "TEA Index" refers the geometric mean tensile energy absorption (having units of g·cm/cm$^2$) at a given geometric mean tensile strength (having units of grams per three inches) as defined by the equation:

$$TEA \text{ Index} = \frac{GM \text{ } TEA \text{ (g·cm/cm}^2\text{)}}{GMT \text{ (g/3")}} \times 100$$

While the TEA Index may vary, in certain instances tissue products prepared according to the present disclosure have a TEA Index greater than about 1.25, such as greater than about 1.50, such as from about 1.25 to about 1.75.

As used herein, the term "Tear Index" refers the geometric mean tear (having units of grams force) at a given geometric mean tensile strength (having units of grams per three inches) as defined by the equation:

$$\text{Tear Index} = \frac{GM\ \text{Tear}\ (gf)}{GMT\ (g/3'')} \times 100$$

While the Tear Index may vary, in certain instances tissue products prepared according to the present disclosure have a Tear Index greater than about 1.50, such as greater than about 1.60, such as greater than about 1.70, such as from about 1.50 to about 2.50, such as from about 1.60 to about 2.25.

As used herein, the term "Burst Index" refers the dry burst strength (having units of grams force) at a given geometric mean tensile strength (having units of grams per three inches) as defined by the equation:

$$\text{Burst Index} = \frac{\text{Dry Burst Strength}\ (gf)}{GMT\ (g/3'')} \times 10$$

While the Burst Index may vary, in certain instances tissue products prepared according to the present disclosure have a Burst Index greater than about 10.0, such as greater than about 10.50, such as greater than about 11.0, such as from about 10.0 to about 12.0.

As used herein the term "Durability Index" refers to the sum of the Tear Index, Burst Index and GM TEA Index, all measured in a dry state, for a given sample. While the Durability Index may vary, in certain instances tissue products prepared according to the present disclosure have a Durability Index greater than about 10.0, such as greater than about 12.0, such as greater than about 14.0, such as from about 10.0 to about 18.0, such as from about 12.0 to about 16.0.

DETAILED DESCRIPTION

In general, the present disclosure is directed to creped tissue webs, and products produced therefrom. The creped webs and products are generally durable, flexible and highly dispersible. For example, the invention provides tissue products having a Slosh time less than 2 minutes, such as less than about 100 seconds, such as less than about 60 seconds, such as less than about 30 seconds, such as from about 10 seconds to 2 minutes, such as from about 10 to about 60 seconds, such as from about 15 to about 45 seconds. Surprisingly, the foregoing Slosh times are achieved despite the tissue products having relatively high cross-machine direction (CD) wet tensile strength, such as greater than about 100 g/3", such as greater than about 115 g/3", such as greater than about 125 g/3", such as from about 100 to about 150 g/3".

In particularly preferred embodiments the present disclosure provides a creped tissue product, such as a multi-ply creped tissue product comprising two or more plies, having a wet CD tensile strength from about 100 to about 150 g/3" and a Slosh time less than 2 minutes, such as less than about 100 seconds, such as less than about 60 seconds, such as less than about 30 seconds, such as from about 10 seconds to 2 minutes, such as from about 10 to about 60 seconds, such as from about 15 to about 45 seconds.

In other embodiments the present invention provides a durable tissue product that retains a relatively high degree of strength when wet and is also highly dispersible. For example, the invention provides creped multi-ply tissue products having a Durability Index greater than about 10.0, a Wet/Dry Ratio greater than about 0.10, such as greater than about 0.125, such as greater than about 0.150 m, and a Slosh time less than about 60 seconds, such as from about 10 to 60 seconds, such as from about 10 to about 45 seconds, such as from about 10 to about 30 seconds.

Figure 9:
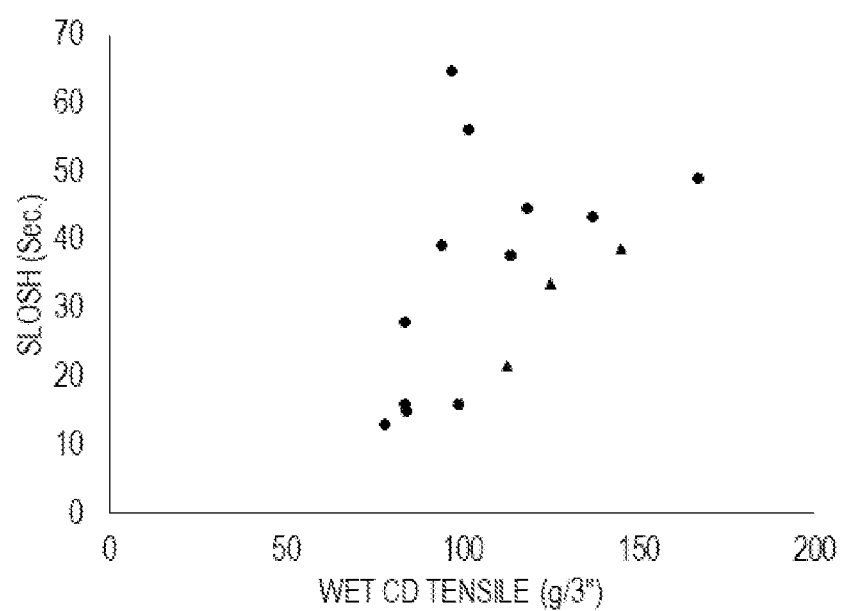
FIG. 9 is a graph of Slosh time (seconds) versus wet CD tensile strength (g/3") for commercial (●) and inventive (▲) products.

A comparison of the Slosh times of several inventive and commercially available tissue products may be found in Table 1, below. As shown in the table below, and in FIG. 9, the inventive tissue products are highly dispersible, having a Slosh time less than about 2 minutes, such as from about 10 seconds to 2 minutes, such as from about 15 seconds to about 60 seconds, despite having a wet CD tensile strength greater than about 100 g/3", and more preferably greater than about 110 g/3", such as from about 110 to about 160 g/3".

TABLE 1

| Sample | Plies | Through-air Dried | Creped | GMT (g/3") | CD Tensile (g/3") | Wet CD Tensile (g/3") | Wet/Dry Ratio | Slosh time (sec) |
|---|---|---|---|---|---|---|---|---|
| Angel Soft | 2 | N | Y | 758 | 715 | 84 | 0.118 | 16 |
| Charmin Sensitive | 2 | Y | Y | 761 | 590 | 102 | 0.173 | 56 |
| Charmin Ultra Soft | 2 | Y | Y | 715 | 468 | 137 | 0.293 | 43 |
| Charmin Ultra Strong | 2 | Y | Y | 1102 | 779 | 167 | 0.215 | 49 |
| Cottonelle Ultra Comfort Care | 2 | Y | N | 990 | 677 | 119 | 0.175 | 45 |
| Great Value Ultra Soft | 2 | Y | Y | 1050 | 844 | 99 | 0.117 | 16 |
| Great Value Ultra Strong | 2 | Y | Y | 1347 | 711 | 94 | 0.132 | 39 |
| Quilted Northern Ultra Soft & Strong | 2 | N | Y | 1286 | 592 | 97 | 0.164 | 65 |
| Target UP & Up Soft | 2 | Y | Y | 802 | 591 | 78 | 0.132 | 13 |
| Target Up & Up Ultra Soft | 2 | Y | Y | 1101 | 788 | 114 | 0.144 | 38 |
| White Cloud Ultra Bath Tissue | 2 | Y | Y | 1212 | 749 | 84 | 0.113 | 15 |
| White Cloud Ultra Soft & Strong | 2 | Y | Y | 1278 | 1021 | 84 | 0.082 | 28 |
| Inventive | 2 | Y | Y | 1380 | 1039 | 288 | 0.277 | 22 |

In other embodiments tissue products prepared according to the present invention not only have good wet strength and dispersability but are also highly durable when dry. For example, multi-ply tissue products prepared according to the present invention generally have a Durability Index greater than about 10.0, such as greater than about 12.0, such as greater than about 14.0, such as from about 10.0 to about 18.0, such as from about 12.0 to about 16.0. The improved durability generally does not come at the expense of product stiffness or dispersability. For example, the tissue products generally have good flexibility, such a Stiffness Index less than about 8.0, such as less than about 6.0, such as less than about 5.5, such as from about 4.0 to about 8.0, such as from about 4.0 to about 6.0 and a Slosh time less than about 2 minutes, such as from about 10 seconds to 2 minutes, such as from about 15 seconds to about 60 seconds.

In a particularly preferred embodiment the invention provides tissue products comprising two or more creped tissue webs, wherein each web comprises a non-crosslinked latex polymer disposed on its outer surface and the product has a Durability Index from about 12.0 to about 16.0, a Stiffness Index from about 4.0 to about 6.0 and a Slosh time from about 15 to about 45 seconds. A comparison of the durability and stiffness of an inventive tissue product to commercially available tissue products may be found in Table 2, below.

TABLE 2

| Sample | Plies | Through-air Dried | Creped | GMT (g/3") | GM TEA (g · cm/cm²) | Stiffness Index | Burst (gf) | GM Tear (gf) | Durability Index |
| --- | --- | --- | --- | --- | --- | --- | --- | --- | --- |
| Angel Soft | 2 | N | Y | 758 | 10.9 | 10.39 | 736 | 13.4 | 12.9 |
| Charmin Sensitive | 2 | Y | Y | 761 | 11.2 | 11.50 | 783 | 17.1 | 14.0 |
| Charmin Ultra Soft | 2 | Y | Y | 715 | 11.7 | 6.94 | 922 | 18.3 | 17.1 |
| Charmin Ultra Strong | 2 | Y | Y | 1102 | 13.3 | 7.12 | 1104 | 21.9 | 13.2 |
| Cottonelle Ultra Comfort Care | 2 | Y | N | 990 | 11.3 | 6.50 | 1120 | 24.4 | 14.9 |
| Great Value Ultra Soft | 2 | Y | Y | 1050 | 8.1 | 10.19 | 741 | 17.4 | 9.5 |
| Great Value Ultra Strong | 2 | Y | Y | 1347 | 11.7 | 6.43 | 942 | 21.7 | 9.5 |
| Quilted Northern Ultra Plush | 3 | N | Y | 665 | 11.4 | 7.43 | 805 | 17.1 | 16.4 |
| Quilted Northern Ultra Soft & Strong | 2 | N | Y | 1286 | 11.4 | 4.56 | 875 | 19.7 | 9.2 |
| Target UP & Up Soft | 2 | Y | Y | 802 | 9.9 | 9.52 | 675 | 18.2 | 11.9 |
| Target Up & Up Ultra Soft | 2 | Y | Y | 1101 | 9.6 | 8.93 | 988 | 19.4 | 11.6 |
| White Cloud Ultra Bath Tissue | 2 | Y | Y | 1212 | 14.5 | 8.80 | 977 | 18.9 | 10.8 |
| White Cloud Ultra Soft & Strong | 2 | Y | Y | 1278 | 14.6 | 7.56 | 1067 | 23.4 | 11.3 |
| Inventive | 2 | Y | Y | 1380 | 30.1 | 5.26 | 1607 | 23.2 | 15.5 |

In other embodiments the invention provides a multi-ply tissue product comprising at least a first and second creped tissue web, wherein the creped tissue webs comprise a non-crosslinked latex polymer disposed on at least one outer surface thereof and at least one of the plies comprises an embossing pattern to provide a visual aesthetic and to enhance the bulk of the product, such that the product has a sheet bulk greater than about 8.0 cc/g, such as greater than about 9.0 cc/g and more preferably greater than about 10.0 cc/g.

In particularly preferred embodiments the tissue products of the present invention comprise a non-crosslinked latex polymer and are treated with a softening composition. For example, the two outer surfaces of the tissue product may comprise a non-crosslinked binder, particularly a vinyl acetate-ethylene polymer, which in certain instances may be carboxylated. In addition to a latex binder, at least one of the outer surfaces further comprises a softening composition selected from the group consisting of a polyhydroxy compound having a molecular weight of at least about 1,000 g/mol, a diamidoamine quaternary compound, an ester quaternary compound, an alkoxy alkyl quaternary compound, a benzyl quaternary compound, an alkyl quaternary compound, an imidazolinium quaternary compounds, a polysiloxane, glycerin, and combinations thereof. The foregoing tissue products generally have good durability, such as a Durability Index greater than about 12.0, low stiffness, such as a Stiffness Index less than about 6.0 and are highly dispersible, such as Slosh time less than about 60 seconds.

In certain embodiments tissue products may be formed from one or more basesheets, which may comprise a single homogenous or blended layer, or be multi-layered. In those instances where the basesheet is multi-layered it may comprise, two, three, or more layers. For example, the basesheet may comprise three layers such as first and second outer layers and a middle layer disposed there between. The layers may comprise the same or different fiber types. For example, the first and second outer layers may comprise short, low coarseness wood pulp fibers, such as hardwood kraft pulp fibers, and the middle layer may comprise long, low coarseness wood pulp fibers, such as northern softwood kraft pulp fibers.

In those instances where the web comprises multiple layers, the relative weight percentage of each layer may vary. For example, the web may comprise first and second outer layers and a middle layer where the first outer layer comprises from about 25 to about 35 weight percent of the layered web, the middle layer comprises from about 30 to about 50 weight percent of the layered web and the second outer layer comprises from about 25 to about 35 weight percent of the layered web.

Multi-layered basesheets useful in the present invention may be formed using any number of different processes known in the art, such as the process disclosed in U.S. Pat. No. 5,129,988, the contents of which are incorporated herein in a manner consistent with the present disclosure. One process for a forming multi-layered basesheet is illustrated in FIG. 1. A dilute aqueous suspension of papermaking fibers is dispersed from a headbox 10 having an upper headbox wall 12 and a lower headbox wall 14 and first and second dividers 16, 18. In this manner the headbox may be used to form a basesheet having outer layers 22, 24 and a middle layer 20, where each of the layers may comprise the same or different papermaking fibers.

To form the multi-layered basesheet, an endless traveling forming fabric 26, suitably supported and driven by rolls 28 and 30, receives the layered papermaking stock issuing from headbox 10. Once retained on fabric 26, the layered fiber suspension passes water through the fabric as shown by the arrows 32. Water removal is achieved by combinations of gravity, centrifugal force and vacuum suction depending on the forming configuration.

In certain embodiments the one or more layers of a multi-layered basesheet, such as the middle layer, may be formed without a substantial amount of inner fiber-to-fiber bond strength. In this regard, the fiber furnish used to form a given layer can be treated with a chemical debonding agent. The debonding agent can be added to the fiber slurry during the pulping process or can be added directly the fiber slurry prior to the headbox. Suitable debonding agents that may be used in the present invention include cationic debonding agents, particularly quaternary ammonium compounds, mixtures of quaternary ammonium compounds with polyhydroxy compounds, and modified polysiloxanes.

Suitable cationic debonding agents include, for example, fatty dialkyl quaternary amine salts, mono fatty alkyl tertiary amine salts, primary amine salts, imidazoline quaternary salts and unsaturated fatty alkyl amine salts. Other suitable debonding agents are disclosed in U.S. Pat. No. 5,529,665, the contents of which are incorporated herein in a manner consistent with the present disclosure. In one embodiment, the debonding agent used in the process of the present invention is an organic quaternary ammonium chloride, such as those available under the tradename ProSoft® (Solenis, Wilmington, DE). The debonding agent can be added to the fiber slurry in an amount of from about 1.0 kg per metric tonne to about 15 kg per metric tonne of fibers present within the slurry.

Particularly useful quaternary ammonium debonders include imidazoline quaternary ammonium debonders, such as oleyl-imidazoline quaternaries, dialkyl dimethyl quaternary debonders, ester quaternary debonders, diamidoamine quaternary debonders, and the like. The imidazoline-based debonding agent can be added in an amount of between 1.0 to about 10 kg per metric tonne.

In other embodiments, a layer or other portion of the basesheet, including the entire basesheet, may optionally include wet or dry strength agents. As used herein, "wet strength agents" are materials used to immobilize the bonds between fibers in the wet state. Any material that when added to the tissue web at an effective level results in providing the basesheet with a wet geometric tensile strength:dry geometric tensile strength ratio in excess of 0.1 will, for purposes of this invention, be termed a wet strength agent. Particularly preferred wet strength agents are temporary wet strength agents. As used herein "temporary wet strength agents" are those which show less than 50 percent of their original wet strength after being saturated with water for five minutes.

Suitable temporary wet strength agents include materials that can react with hydroxyl groups, such as on cellulosic pulp fibers, to form hemiacetal bonds that are reversible in the presence of excess water. Suitable temporary wet strength agents are known to those of ordinary skill in the art. Non-limiting examples of temporary wet strength agents suitable for the fibrous structures of the present invention include glyoxalated polyacrylamide polymers, for example cationic glyoxalated polyacrylamide polymers. Temporary wet strength agents useful in the present invention may have average molecular weights of from about 20,000 to about 400,000, such as from about 50,000 to about 400,000, such as from about 70,000 to about 400,000, such as from about 70,000 to about 300,000, such as about 100,000 to about 200,000. In certain instances the temporary wet strength agent may comprise a commercially available temporary wet strength agent such as those marketed under the tradename Hercobond® (Solenis, Wilmington, DE) or Fenno-Bond® (Kemira Chemicals, Inc., Atlanta, GA).

In other instances, the basesheet may optionally include a dry strength additive, such as carboxymethyl cellulose resins, starch based resins, and mixtures thereof. Particularly preferred dry strength additives are cationic starches, and mixtures of cationic and anionic starches. In certain instances the dry strength agent may comprise a commercially available modified starch such as marketed under the tradename RediBOND® (Ingredion, Westchester, IL) or a commercially available carboxymethyl cellulose resin such as those marketed under the tradename Aqualon® (Ashland LLC, Bridgewater, NJ).

The amount of wet strength agent or dry strength added to the pulp fibers can be at least about 0.1 dry weight percent, more specifically about 0.2 dry weight percent or greater, and still more specifically from about 0.1 to about 3 dry weight percent, based on the dry weight of the fibers.

Tissue basesheets useful in forming tissue products of the present invention may be formed using any one of several well-known manufacturing processes. For example, in certain embodiments, tissue products may be produced by a through-air drying (TAD) manufacturing process, an advanced tissue molding system (ATMOS) manufacturing process, a structured tissue technology (STT) manufacturing process, a conventional wet pressed (also referred to as "CTEC") manufacturing process or a belt creped manufacturing process. In particularly preferred embodiments the tissue product is manufactured by a creped through-air dried (CTAD) process or uncreped through-air dried (UCTAD) process.

Figure 2:
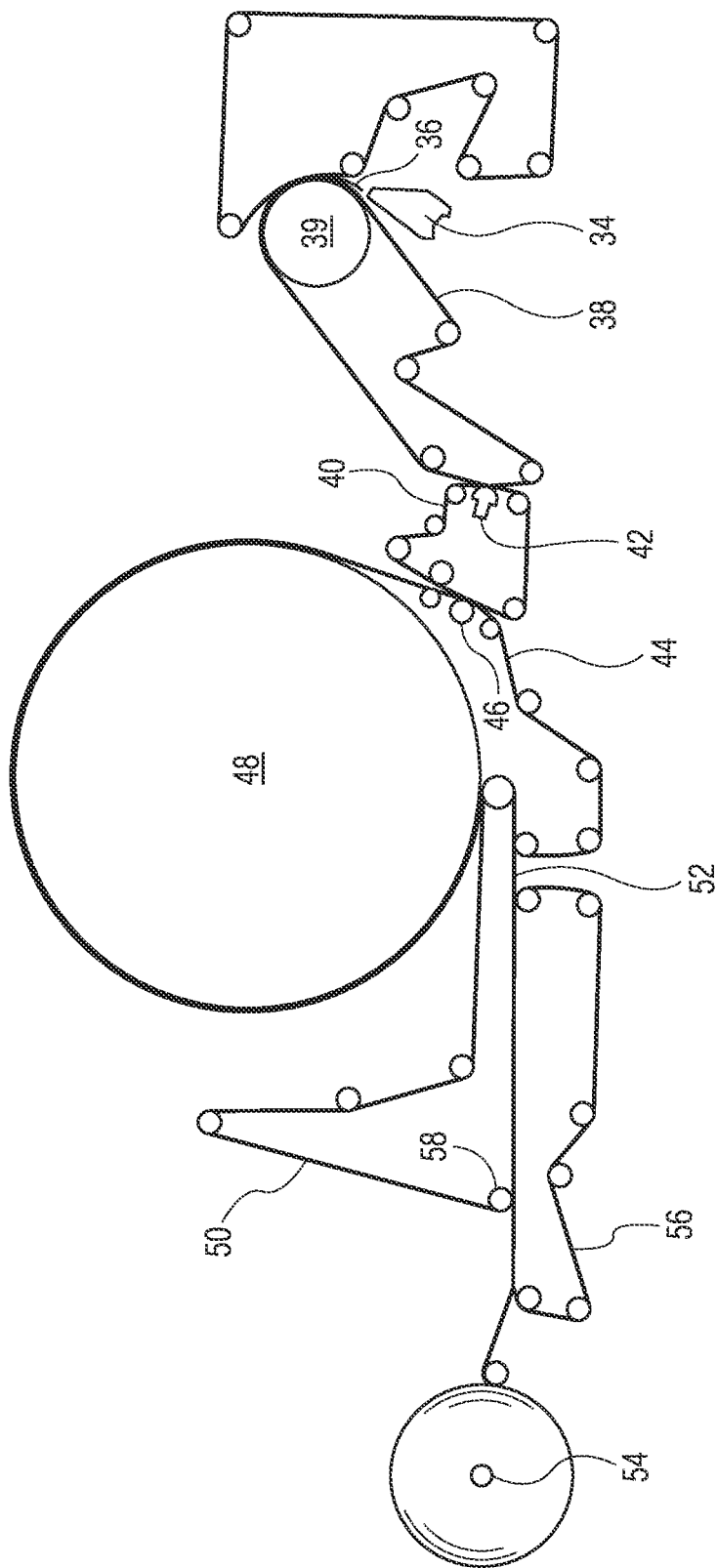
FIG. 2 illustrates one embodiment for forming a basesheet useful in the production of a tissue product according to the present invention.

With reference now to FIG. 2, a method for making through-air dried paper sheets is illustrated. Shown is a twin wire former having a papermaking headbox 34, such as a layered headbox, which injects or deposits a stream 36 of an aqueous suspension of papermaking fibers onto the forming fabric 38 positioned on a forming roll 39. The forming fabric serves to support and carry the newly-formed wet web downstream in the process as the web is partially dewatered to a consistency of about 10 dry weight percent. Additional dewatering of the wet web can be carried out, such as by vacuum suction, while the wet web is supported by the forming fabric.

The wet web is then transferred from the forming fabric to a transfer fabric 40. In one embodiment, the transfer fabric can be traveling at a slower speed than the forming fabric in order to impart increased stretch into the web. This is commonly referred to as a "rush" transfer. The relative speed difference between the two fabrics can be from 0 to 60 percent, more specifically from about 15 to 45 percent. Transfer is preferably carried out with the assistance of a vacuum shoe 42 such that the forming fabric and the transfer fabric simultaneously converge and diverge at the leading edge of the vacuum slot.

The web is then transferred from the transfer fabric to the through-air drying fabric 44 with the aid of a vacuum transfer roll 46 or a vacuum transfer shoe, optionally again using a fixed gap transfer as previously described. The through-air drying fabric can be traveling at about the same speed or a different speed relative to the transfer fabric. If desired, the through-air drying fabric can be run at a slower speed to further enhance stretch. Transfer can be carried out with vacuum assistance to ensure deformation of the sheet to conform to the through-air drying fabric, thus yielding desired bulk and imparting the web with a three-dimensional topographical pattern. Suitable through-air drying fabrics are described, for example, in U.S. Pat. Nos. 6,998,024, 7,611,607 and 10,161,084, the contents of which are incorporated herein by reference in a manner consistent with the present disclosure.

In one embodiment, the through-air drying fabric comprises a single layer fabric woven from shute and warp filaments. In certain instances, the shute filaments may comprise two or more different diameters and may be interwoven with the warp filaments so as to form a textured sheet contacting surface having substantially continuous machine-direction ripples separated by valleys. In other instances, the woven fabric may comprise a plurality of substantially continuous machine-direction ripples formed of multiple warp strands grouped together and supported by multiple shute strands of two or more diameters. During drying, the web can be macroscopically arranged to conform to the surface of the through-air drying fabric and form a textured, three-dimensional surface.

The side of the web contacting the through-air drying fabric is typically referred to as the "fabric side" of the paper web. The fabric side of the paper web, as described above, may have a shape that conforms to the surface of the through-air drying fabric after the fabric is dried in the through-air dryer. The opposite side of the paper web, on the other hand, is typically referred to as the "air side."

The level of vacuum used for the web transfers can be from about 3 to about 15 inches of mercury (75 to about 380 millimeters of mercury), preferably about 5 inches (125 millimeters) of mercury. The vacuum shoe (negative pressure) can be supplemented or replaced by the use of positive pressure from the opposite side of the web to blow the web onto the next fabric in addition to or as a replacement for sucking it onto the next fabric with vacuum. Also, a vacuum roll or rolls can be used to replace the vacuum shoe(s).

While supported by the through-air drying fabric, the web is dried to a consistency of about 94 percent or greater by the through-air dryer 48 and thereafter transferred to a carrier fabric 50. The dried basesheet 52 is transported to the reel 54 using carrier fabric 50 and an optional carrier fabric 56. An optional pressurized turning roll 58 can be used to facilitate transfer of the web from carrier fabric 50 to fabric 56.

In one embodiment, the reel 54 shown in FIG. 2 can run at a speed slower than the fabric 56 in a rush transfer process for building bulk into the paper web 52. For instance, the relative speed difference between the reel and the fabric can be from about 5 to about 25 percent and, particularly from about 12 to about 14 percent. Rush transfer at the reel can occur either alone or in conjunction with a rush transfer process upstream, such as between the forming fabric and the transfer fabric.

Once the web is formed, a binder composition is applied to at least one side of the web. In this manner, the present invention provides a tissue product comprising a web having first and second outer surfaces, wherein at least one outer surface comprises a topically-applied binder, particularly a binder applied in a network. As used herein, the term "network" is used to describe any binder pattern that serves to bond the sheet together. The pattern can be regular or irregular and can be continuous or discontinuous.

Figure 3:
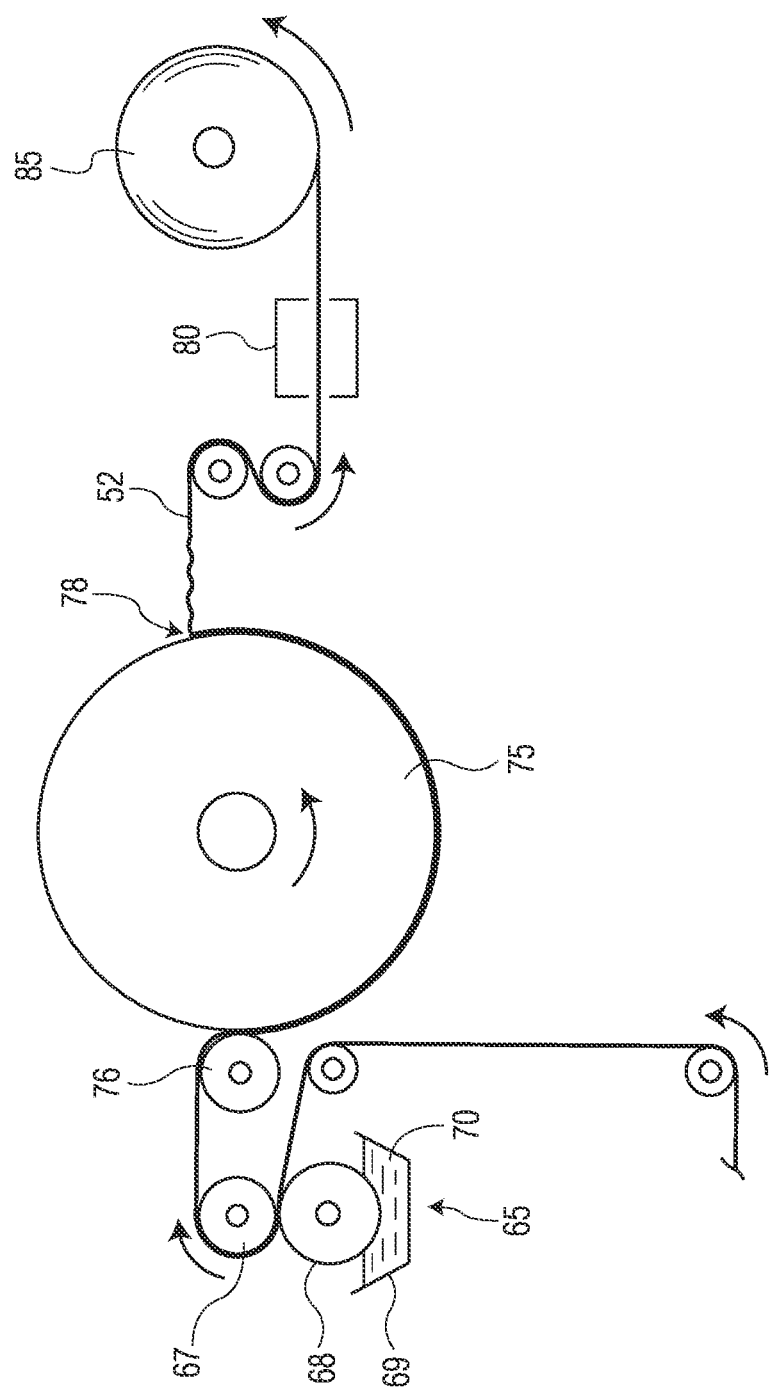
FIG. 3 illustrates one embodiment of a print-crepe process for producing a tissue product according to the present invention.

With reference now to FIG. 3, one embodiment of applying a binder material to one outer surface of a web is illustrated. Shown is paper web 52 passing through a binder material application station 65. Station 65 includes a transfer roll 67 in contact with a rotogravure roll 68, which is in communication with a reservoir 69 containing a suitable binder 70. Although gravure printing of the binder is illustrated, other means of applying the binder material can also be used, such as foam application, spray application, flexographic printing, or digital printing methods, such as ink jet printing, and the like. The rotogravure roll 68 applies binder material 70 to one side of the web 52 in a pre-selected pattern.

Figure 4:
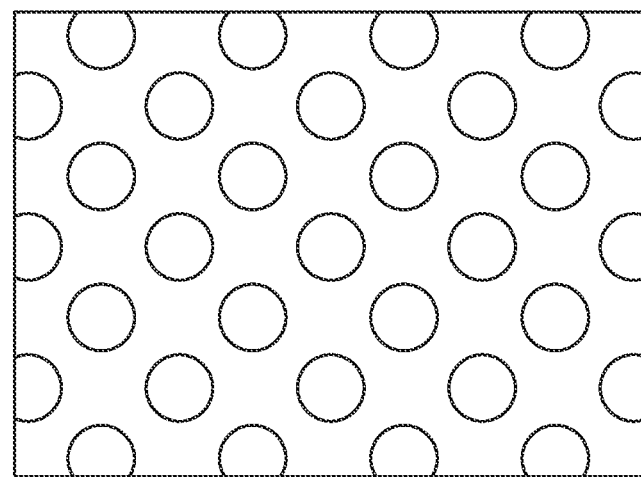
FIG. 4 illustrates one pattern for applying a binder to a basesheet.
Figure 5:
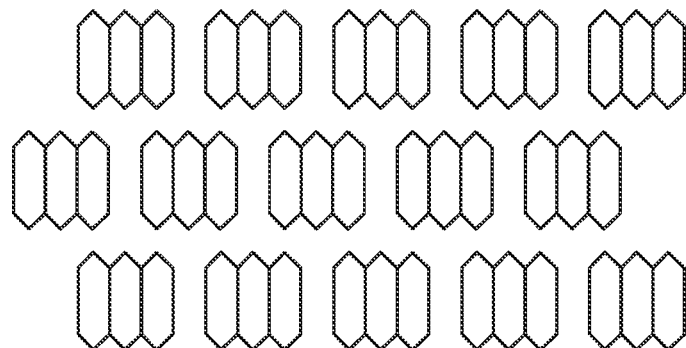
FIG. 5 illustrates another pattern for applying a binder to a basesheet.
Figure 6:
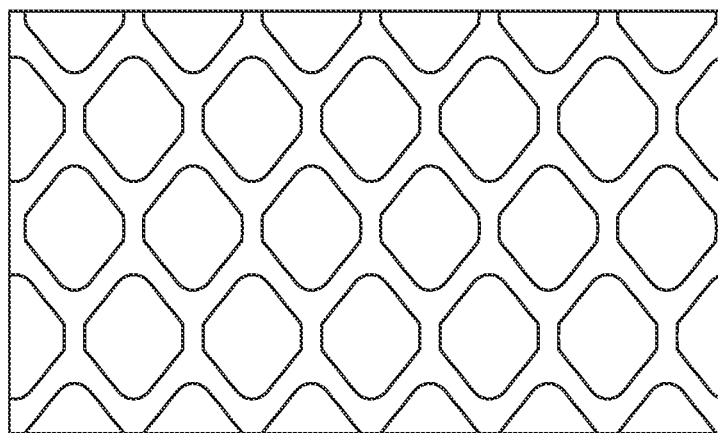
FIG. 6 illustrates still another pattern for applying a binder to a basesheet.
Figure 7:
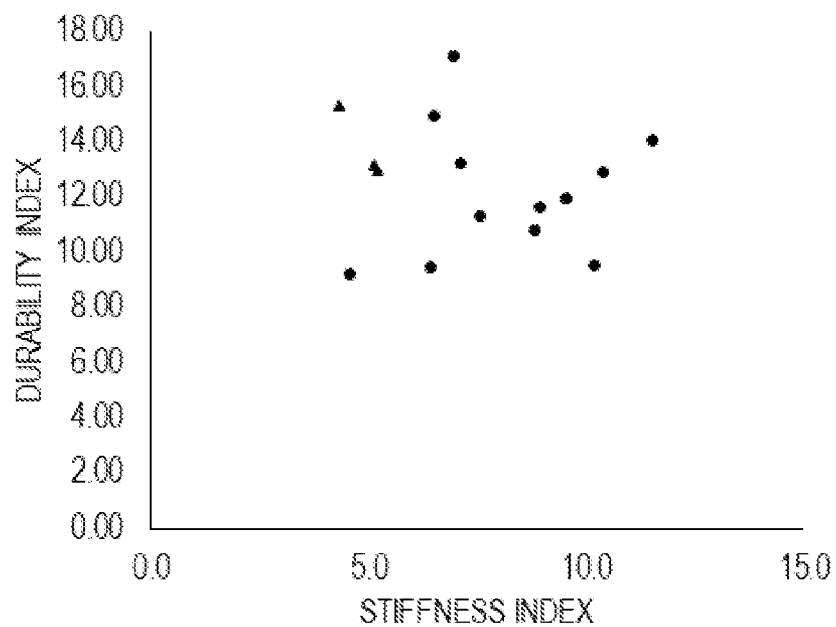
FIG. 7 is a graph of Durability Index versus Stiffness Index for commercial (●) and inventive (▲A) products.
Figure 8:
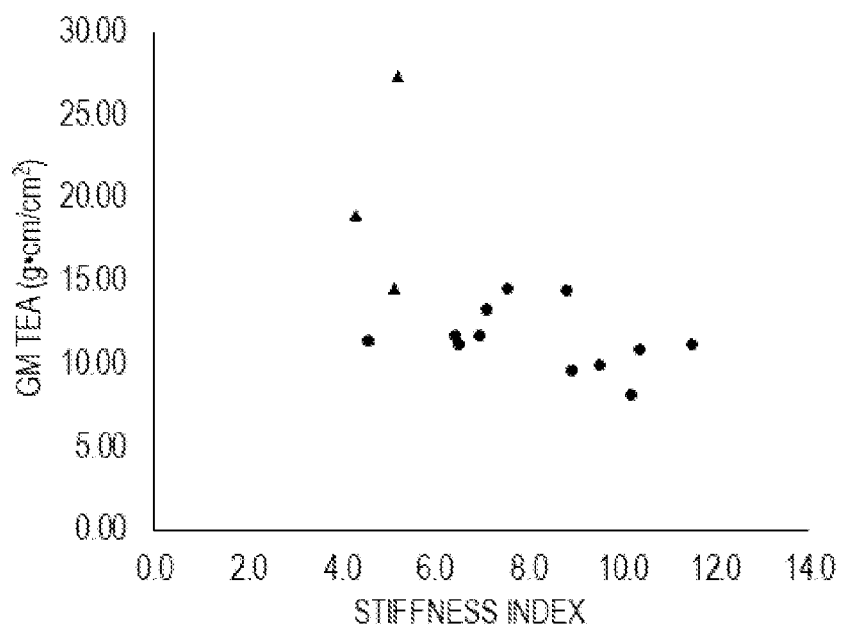
FIG. 8 is a graph of GM TEA versus Stiffness Index for commercial (●) and inventive (▲) products.

FIGS. 4-6 illustrate several different print patterns that may be used for applying a binder material to a basesheet in accordance with this invention. As illustrated in FIG. 4, the pattern may comprise a succession of discrete dots. In one embodiment, for instance, the dots can be spaced so that there are approximately from about 25 to about 35 dots per inch (25.4 mm) in the machine direction and/or the cross-machine direction. The dots can have a diameter, for example, of from about 0.01 inch (0.25 mm) to about 0.03 inch (0.76 mm). In one particular embodiment, the dots can have a diameter of about 0.02 inch (0.51 mm) and can be present in the pattern so that approximately 28 dots per inch (25.4 mm) extend in both the machine direction and the cross-machine direction. Besides dots, various other discrete shapes such as elongated ovals or rectangles can also be used when printing the binder material onto the sheet.

FIG. 5 shows a print pattern in which the binder material print pattern is made up of discrete multiple deposits that are each comprised of three elongated hexagons. In one embodiment, each hexagon can be about 0.02 inch (0.51 mm) long and can have a width of about 0.006 inch (0.15 mm). Approximately 35 to 40 deposits per inch (25.4 mm) can be spaced in the machine direction and the cross-machine direction.

FIG. 6 illustrates an alternative binder material pattern in which the binder material is printed onto the sheet in a reticulated pattern. The dimensions are similar to those of the dot pattern of FIG. 4. Reticulated patterns, which provide a continuous network of binder material, may result in relatively greater sheet strength than comparable patterns of discrete elements, such as the dot pattern of FIG. 4. It will be appreciated that many other patterns, in addition to those illustrated above, can also be used depending on the desired properties of the final product.

With reference again to FIG. 3, after the binder material 70 is applied, the sheet 52 is adhered to a heated creping cylinder 75 by a press roll 76. The sheet 52 is carried on the surface of the heated creping cylinder 75 for a distance and then removed therefrom by the action of a creping blade 78. The creping blade 78 performs a controlled pattern creping operation on the side of the sheet 52 to which the binder material 70 was applied.

Once creped, the sheet 52 is pulled through an optional drying station 80. The drying station can include any form of a heating unit, such as an oven energized by infrared heat, microwave energy, hot air, or the like. Alternatively, the drying station may comprise other drying methods such as photo-curing, UV-curing, corona discharge treatment, electron beam curing, curing with reactive gas, curing with heated air such as through-air heating or impingement jet heating, infrared heating, contact heating, inductive heating, microwave or RF heating, and the like. Depending upon the binder material selected, however, drying station 80 may not be needed. Once passed through the drying station 80, the sheet 52 can be wound into a roll of material or product 85.

In certain instances the binder composition may be selected not only to assist in creping the web but also for improving one or more physical properties of the web such as, for example, dry strength, wet strength, stretchability, and tear resistance. Particular binder compositions that may be used in the present invention include latex compositions. The latex composition may comprise a non-carboxylated latex emulsion or a carboxyl-functional latex emulsion polymer. Non-carboxylated latex emulsions useful in the present invention may comprise an aqueous polymer dispersion of vinyl acetate and ethylene. Suitable non-carboxylated latex emulsions include vinyl acetate and ethylene emulsions such as Vinnapas® EZ123, commercially available from Wacker Polymers, LP (Allentown, PA). In other instances the binder composition may comprise a carboxyl-functional latex polymers such as Vinnapas® EP1133, commercially available from Wacker Polymers, LP (Allentown, PA).

Latex polymers useful in the present invention may comprise unsaturated monomers, such as vinyl acetate and ethylene monomers, polymerized in the presence of surfactants and initiators to produce emulsion-polymerized polymer particles. Unsaturated monomers contain carbon-to-carbon double bond unsaturation and generally include vinyl monomers, styrenic monomers, acrylic monomers, allylic monomers, acrylamide monomers, as well as carboxyl functional monomers. Vinyl monomers include vinyl esters such as vinyl acetate, vinyl propionate and similar vinyl lower alkyl esters, vinyl halides, vinyl aromatic hydrocarbons such as styrene and substituted styrenes, vinyl aliphatic monomers such as alpha olefins and conjugated dienes, and vinyl alkyl ethers such as methyl vinyl ether and similar vinyl lower alkyl ethers. Acrylic monomers include lower alkyl esters of acrylic or methacrylic acid having an alkyl ester chain from one to twelve carbon atoms as well as aromatic derivatives of acrylic and methacrylic acid. Useful acrylic monomers include, for instance, methyl, ethyl, butyl, and propyl acrylates and methacrylates, 2-ethyl hexyl acrylate and methacrylate, cyclohexyl, decyl, and isodecyl acrylates and methacrylates, and similar various acrylates and methacrylates.

In certain embodiments the latex polymers may comprise a carboxyl-functional latex polymer comprising copolymerized carboxyl-functional monomers such as acrylic and methacrylic acids, fumaric or maleic or similar unsaturated dicarboxylic acids, where the preferred carboxyl monomers are acrylic and methacrylic acid. In certain instances the carboxyl-functional latex polymers may comprise by weight from about 1 to about 50 percent copolymerized carboxyl monomers with the balance being other copolymerized ethylene monomers. Suitable carboxyl-functional latex polymers include carboxylated vinyl acetate-ethylene polymer emulsions such as Vinnapas® EP1133, commercially available from Wacker Polymers, LP (Allentown, PA).

In certain instances the binder composition may optionally contain an anti-blocking additive designed to modify the surface chemistry or characteristics of the binder film on the basesheet. Suitable anti-blocking additives generally do not react chemically with the binder and may include: 1) surfactants, including anionic surfactants such as sodium and potassium salts of stearic, palmitic, oleic, lauric, and tall oil fatty acids, and non-ionic surfactants such as polyoxyethylene glycols reacted to a lyophilic compound; 2) non-reactive additives, such as silicones, waxes, oils, designed to modify the surface chemistry of at least one outer surface of the web to reduce blocking; and 3) soluble or insoluble crystals, such as sugars, talc, clay, and the like, designed to reside on the surface of the binder film and thus reduce its propensity to cause blocking to an adjacent web surface. The amount of the anti-blocking additive in the binder composition, relative to the amount of carboxyl-functional latex emulsion polymer on a weight percent solids basis, can be from about 1 to about 25 percent, more specifically from about 5 to about 20 percent and more specifically from about 10 to about 15 percent.

Accordingly, in certain embodiments, binders useful in the present invention may consist essentially of a non-crosslinked latex polymer, such as a vinyl acetate-ethylene latex polymer, and optionally an anti-blocking agent, such as a polysaccharide, to prevent blocking upon drying of the tissue web.

In certain preferred embodiments it may be desirable to form the inventive tissue products using a binder that is substantially free from polyfunctional aldehydes, such as glyoxalated polyacrylamide and glyoxal, and azetidinium-functional cross-linking polymers, such as polyamide-epichlorohydrin (PAE) resins and polyamide-polyamine-epichlorohydrin (PPE) resins. Thus, in a preferred embodiment the latex polymer, which may comprise either a non-carboxylated or a carboxylated latex polymer, is not subjected to crosslinking before or after it is applied to the tissue web.

In certain instances, the binder composition may be applied to the base web in a preselected pattern. In one embodiment, for instance, the binder composition can be applied to the web in a reticular pattern, such that the pattern is interconnected forming a net-like design or grid on the surface. In other embodiments the binder composition may be applied to the web in a pattern that represents a succession of discrete shapes. For example, the binder composition may be applied in a pattern of discrete dots. Despite consisting of discrete shapes, such patterns provide the desired physical properties without covering a substantial portion of the surface area of the web.

In certain preferred embodiments the binder composition is applied to only one side of the web so as to cover from about 15 to about 75 percent of the surface area of the web. More particularly, in most applications, the binder composition will cover from about 20 to about 60 percent of the surface area of the web. The total amount of binder composition applied to the web can be in the range of from about 1 to about 25 percent by weight, such as from about 2 to about 10 percent by weight, based upon the total weight of the web.

In the embodiment shown in FIG. 3 only one side of the web is treated with a binder composition leaving an untreated side. Leaving one side of the tissue web untreated may provide various benefits and advantages under some circumstances. For instance, the untreated side may increase the ability of the tissue web to absorb liquids faster. Further, the untreated side may have a greater texture than if the side were treated with a binder composition.

Further, the process illustrated in FIG. 3 represents only one possible method for applying a binder composition to the web. Other applications methods may be suitable for applying a binder composition to the web. For example, various printing methods can be used to print the binder composition onto the web depending upon the particular application. Such printing methods can include direct gravure printing, offset gravure printing, or flexographic printing.

In addition to having a binder composition applied to one or more outer surfaces, as described above, the tissue product may be subjected to additional converting, such as calendering, treatment with a softening composition, embossing, slitting, winding and/or folding.

In certain embodiments tissue products of the present invention may be treated with a softening composition to improve the hand feel or deliver a benefit to the end user. As used herein, the term "softening composition" refers to any chemical composition which improves the tactile sensation perceived by the end user who holds a particular tissue product and rubs it across the skin. Suitable softening compositions include, for example, basic waxes such as paraffin and beeswax and oils such as mineral oil and silicone oil as well as petrolatum and more complex lubricants and emollients such as quaternary ammonium compounds with long alkyl chains, functional silicones, fatty acids, fatty alcohols and fatty esters.

Accordingly, in one embodiment the tissue products of the present invention may be treated with a softening composition comprising one or more oils, such as mineral oil, waxes, such as paraffin, or plant extracts, such as chamomile and aloe vera, such as disclosed in U.S. Pat. Nos. 5,885,697 and 5,525,345, the contents of which are incorporated herein in a manner consistent with the present disclosure.

In other embodiments the tissue products may be treated with a softening composition comprising a polysiloxane, and more preferably with a composition comprising an amino-functional polysiloxane, a surfactant and optionally a skin conditioning agent, such as the compositions disclosed in U.S. Publication No. 2006/0130989, the contents of which are incorporated herein in a manner consistent with the present disclosure. In certain preferred embodiments the polysiloxane is an amino-functional polysiloxane, the surfactant is an ethoxylated alcohol or an ethoxylated propoxylated alcohol and the skin conditioning agent is vitamin E and/or aloe vera.

In still other embodiments the tissue products may be treated with a softening composition comprising a cationic softening compound and a relatively high molecular weight polyhydroxy compound. Suitable cationic softening compounds include both quaternary ammonium compounds including, for example, amidoamine quaternary ammonium compounds, diamidoamine quaternary ammonium compounds, ester quaternary ammonium compounds, alkoxy alkyl quaternary ammonium compounds, benzyl quaternary ammonium compounds, alkyl quaternary ammonium compounds, and imidazolinium compounds. Examples of polyhydroxy compounds useful in the present invention include, but are not limited to, polyethylene glycols and polypropylene glycols having a molecular weight of at least about 1,000 g/mol and more preferably greater than about 2,000 g/mol and still more preferably greater than about 4,000 g/mol and more preferably greater than about 6,000 g/mol, such as from about 1,000 to about 12,000 g/mol, and more preferably from about 4,000 to about 10,000 g/mol and still more preferably from about 6,000 to about 8,000 g/mol.

In yet other embodiments the softening composition may comprise a cationic softening compound, a relatively high molecular weight polyhydroxy compound and polysiloxane. Any polysiloxane capable of enhancing the tactile softness of the tissue sheet is suitable for incorporation in this manner so long as solutions or emulsions of the cationic softener, polyhydroxy and silicone are compatible, that is when mixed they do not form gels, precipitates or other physical defects that would preclude application to the tissue sheet.

In other embodiments softening compositions useful in the present invention may consist essentially of water, a cationic softening compound, such as a quaternary ammonium compound, a polyhydroxy compound having a molecular weight of at least about 1,000 g/mol and optionally a silicone or glycerin, or mixtures thereof. In other embodiments the softening composition may consist essentially of water, a quaternary ammonium compound, a polyhydroxy compound having a molecular weight of at least about 1,000 g/mol, a silicone and glycerin. When incorporated in the softening composition, the amount of glycerin in the softening composition can be from about 5.0 to about 40 weight percent, more particularly from about 10 to about 30 weight percent, and still more particularly from about 15 to about 20 weight percent.

All of the foregoing softening compositions may optionally contain a beneficial agent, such as a skin conditioning agent or a humectant, which may be provided in an amount ranging from about 0.01 to about 5 percent by weight of the composition. Suitable humectants include lactic acid and its salts, sugars, ethoxylated glycerin, ethoxylated lanolin, corn syrup, hydrolyzed starch hydrolysate, urea, and sorbitol. Suitable skin conditioning agents include allantoin, kaolin, zinc oxide, aloe vera, vitamin E, petrolatum and lanolin. Again, the foregoing additives are generally complementary to the softening compositions of the present invention and generally do not significantly and adversely affect important tissue product properties, such as strength or absorbency of the tissue product, or negatively affect the softening provided by the softening compositions of the present invention.

The foregoing softening compositions are generally applied to one or two outermost surfaces of a dry tissue web and more preferably a creped tissue web having a binding composition disposed on at least one outer surface. The method by which the softening composition is applied to the tissue sheet may be accomplished by any method known in the art. For example, in one embodiment the composition may be applied by contact printing methods such as gravure, offset gravure, flexographic printing, and the like. The contact printing methods often enable topical application of the composition to the tissue sheet. In other embodiments the softening composition may be applied to the tissue web by non-contact printing methods such as ink jet printing, digital printing of any kind, and the like.

In certain preferred embodiments the softening composition may be prepared as an aqueous solution and applied to the web by spraying or rotogravure printing. It is believed in this manner that tactile softness of the tissue sheet and resulting tissue products may be improved due to presence of the softening composition on the surface of the tissue product. When applied as an aqueous solution, the softening composition may comprise from about 50 to about 90 weight percent, by weight of the composition, water and more preferably from about 60 to about 80 percent.

In other instances the basesheets prepared as described above may be subjected to embossing and plying to produce the inventive tissue products. For example, the tissue products of the present invention may be provided as multi-ply products comprising two or more plies, such as two, three or four plies, where the plies are embossed and laminated together. In one embodiment, the multi-ply product of the present invention may be produced using an embossing-laminating device, such as those described in U.S. Pat. Nos. 3,556,907, 3,867,225 and 5,339,730, the contents of which are incorporated herein in a manner consistent with the present disclosure. For example, two plies may be embossed separately, each between an embossing roller and a counter-roller or pressure roller. The two plies may then be brought into facing relation with one another and joined so that the protuberances of one ply are nested between the protuberances of the other ply. Typically, lamination of the two plies is obtained between one of the embossing rollers and a laminating roller, while the two embossing rollers do not touch.

Test Methods

Basis Weight

Prior to testing, all samples are conditioned under TAPPI conditions (23±1° C. and 50±2 percent relative humidity) for a minimum of 4 hours. Basis weight of sample is measured by selecting twelve (12) products (also referred to as sheets) of the sample and making two (2) stacks of six (6) sheets. In the event the sample consists of perforated sheets of bath or towel tissue, the perforations must be aligned on the same side when stacking the usable units A precision cutter is used to cut each stack into exactly 10.16×10.16 cm (4.0×4.0 inch) squares. The two stacks of cut squares are combined to make a basis weight pad of twelve (12) squares thick. The basis weight pad is then weighed on a top loading balance with a minimum resolution of 0.01 grams. The top loading balance must be protected from air drafts and other disturbances using a draft shield. Weights are recorded when the readings on the top loading balance become constant. The mass of the sample (grams) per unit area (square meters) is calculated and reported as the basis weight, having units of grams per square meter (gsm).

Caliper

Caliper is measured in accordance with TAPPI test methods Test Method T 580 pm-12 "Thickness (caliper) of towel, tissue, napkin and facial products." The micrometer used for carrying out caliper measurements is an Emveco 200-A Tissue Caliper Tester (Emveco, Inc., Newberg, OR). The micrometer has a load of 2 kilo-Pascals, a pressure foot area of 2,500 square millimeters, a pressure foot diameter of 56.42 millimeters, a dwell time of 3 seconds and a lowering rate of 0.8 millimeters per second.

Burst Strength (Wet or Dry)

Burst Strength is measured using an EJA Burst Tester (series #50360, commercially available from Thwing-Albert Instrument Company, Philadelphia, PA). The test procedure is according to TAPPI T570 pm-00 except the test speed. The test specimen is clamped between two concentric rings whose inner diameter defines the circular area under test. A penetration assembly, the top of which is a smooth, spherical steel ball, is arranged perpendicular to and centered under the rings holding the test specimen. The penetration assembly is raised at 6 inches per minute such that the steel ball contacts and eventually penetrates the test specimen to the point of specimen rupture. The maximum force applied by the penetration assembly at the instant of specimen rupture is reported as the burst strength in grams force (gf) of the specimen.

The penetration assembly consists of a spherical penetration member which is a stainless steel ball with a diameter of 0.625±0.002 inches (15.88±0.05 mm) finished spherical to 0.00004 inches (0.001 mm). The spherical penetration member is permanently affixed to the end of a0.375±0.010 inch (9.525±0.254 mm) solid steel rod. A 2000 gram load cell is used and 50 percent of the load range i.e. 0-1000 g is selected. The distance of travel of the probe is such that the upper most surface of the spherical ball reaches a distance of 1.375 inches (34.9 mm) above the plane of the sample clamped in the test. A means to secure the test specimen for testing consisting of upper and lower concentric rings of approximately 0.25 inches (6.4 mm) thick aluminum between which the sample is firmly held by pneumatic clamps operated under a filtered air source at 60 psi. The clamping rings are 3.50±0.01 inches (88.9±0.3 mm) in internal diameter and approximately 6.5 inches (165 mm) in outside diameter. The clamping surfaces of the clamping rings are coated with a commercial grade of neoprene approximately 0.0625 inches (1.6 mm) thick having a Shore hardness of 70-85 (A scale). The neoprene needs not cover the entire surface of the clamping ring but is coincident with the inner diameter, thus having an inner diameter of 3.50±0.01 inches (88.9±0.3 mm) and is 0.5 inches (12.7 mm) wide, thus having an external diameter of 4.5±0.01 inches (114±0.3 mm). For each test a total of 3 sheets of product are combined.

The sheets are stacked on top of one another in a manner such that the machine direction of the sheets is aligned. Where samples comprise multiple plies, the plies are not separated for testing. In each instance the test sample comprises 3 sheets of product. For example, if the product is a 2-ply tissue product, 3 sheets of product, totaling 6 plies are tested. If the product is a single ply tissue product, then 3 sheets of product totaling 3 plies are tested.

Samples are conditioned under TAPPI conditions and cut into 127×127±5 mm squares. For wet burst measurement, after conditioning the samples were wetted for testing with 0.5 mL of deionized water dispensed with an automated pipette. The wet sample is tested immediately after insulting.

The peak load (gf) and energy to peak (g-cm) are recorded and the process repeated for all remaining specimens. A minimum of five specimens are tested per sample and the peak load average of five tests is reported.

Tear

Tear testing was carried out in accordance with TAPPI test method T-414 "Internal Tearing Resistance of Paper (Elmendorf-type method)" using a falling pendulum instrument such as Lorentzen & Wettre Model SE 009. Tear strength is directional, and MD and CD tear are measured independently.

More particularly, a rectangular test specimen of the sample to be tested is cut out of the tissue product or tissue base sheet such that the test specimen measures 63±0.15 mm (2.5±0.006 inches) in the direction to be tested (such as the MD or CD direction) and between 73 and 114 mm (2.9 and 4.6 inches) in the other direction. The specimen edges must be cut parallel and perpendicular to the testing direction (not skewed). Any suitable cutting device, capable of the prescribed precision and accuracy, can be used. The test specimen should be taken from areas of the sample that are free of folds, wrinkles, crimp lines, perforations or any other distortions that would make the test specimen abnormal from the rest of the material.

The number of plies or sheets to test is determined based on the number of plies or sheets required for the test results to fall between 20 to 80 percent on the linear range scale of the tear tester and more preferably between 20 to 60 percent of the linear range scale of the tear tester. The sample preferably should be cut no closer than 6 mm (0.25 inch) from the edge of the material from which the specimens will be cut. When testing requires more than one sheet or ply the sheets are placed facing in the same direction.

The test specimen is then placed between the clamps of the falling pendulum apparatus with the edge of the specimen aligned with the front edge of the clamp. The clamps are closed and a 20-millimeter slit is cut into the leading edge of the specimen usually by a cutting knife attached to the instrument. For example, on the Lorentzen & Wettre Model SE 009 the slit is created by pushing down on the cutting knife lever until it reaches its stop. The slit should be clean with no tears or nicks as this slit will serve to start the tear during the subsequent test.

The pendulum is released and the tear value, which is the force required to completely tear the test specimen, is recorded. The test is repeated a total of ten times for each sample and the average of the ten readings reported as the tear strength. Tear strength is reported in units of grams of force (gf). The average tear value is the tear strength for the direction (MD or CD) tested. The "geometric mean tear strength" is the square root of the product of the average MD tear strength and the average CD tear strength. The Lorentzen & Wettre Model SE 009 has a setting for the number of plies tested. Some testers may need to have the reported tear strength multiplied by a factor to give a per ply tear strength. For base sheets intended to be multiple ply products, the tear results are reported as the tear of the multiple ply product and not the single ply base sheet. This is done by multiplying the single ply base sheet tear value by the number of plies in the finished product. Similarly, multiple ply finished product data for tear is presented as the tear strength for the finished product sheet and not the individual plies. A variety of means can be used to calculate but in general will be done by inputting the number of sheets to be tested rather than the number of plies to be tested into the measuring device. For example, two sheets would be two 1-ply sheets for 1-ply product and two 2-ply sheets (4-plies) for 2-ply products.

Tensile

Tensile testing is conducted on a tensile testing machine maintaining a constant rate of elongation and the width of each specimen tested is 3 inches. More specifically, samples for dry tensile strength testing were prepared by cutting a 3±0.05 inches (76.2±1.3 mm) wide strip in either the machine direction (MD) or cross-machine direction (CD) orientation using a JDC Precision Sample Cutter (Thwing-Albert Instrument Company, Philadelphia, PA, Model No. JDC 3-10, Serial No. 37333) or equivalent. The instrument used for measuring tensile strengths was an MTS Systems Sintech 11S, Serial No. 6233. The data acquisition software was MTS TestWorks® for Windows Ver. 3.10 (MTS Systems Corp., Research Triangle Park, NC). The load cell was selected from either a 50 Newton or 100 Newton maximum, depending on the strength of the sample being tested, such that the majority of peak load values fall between 10 to 90 percent of the load cell's full scale value. The gauge length between jaws was 4±0.04 inches (101.6±1 mm) for facial tissue and towels and 2±0.02 inches (50.8±0.5 mm) for bath tissue. The crosshead speed was 10±0.4 inches/min (254±1 mm/min), and the break sensitivity was set at 65 percent. The sample was placed in the jaws of the instrument, centered both vertically and horizontally. The test was then started and ended when the specimen broke. The peak load was recorded as either the "MD tensile strength" or the "CD tensile strength" of the specimen depending on direction of the sample being tested. Ten representative specimens were tested for each product or sheet and the arithmetic average of all individual specimen tests was recorded as the appropriate MD or CD tensile strength having units of grams per three inches (g/3"). Tensile energy absorbed (TEA) and slope are also calculated by the tensile tester. TEA is reported in units of g·cm/cm$^2$ and slope is recorded in units of kilograms (kg). Both TEA and Slope are directionally dependent and thus MD and CD directions are measured independently.

All products were tested in their product forms without separating into individual plies. For example, a 2-ply product was tested as two plies and recorded as such. In the tensile properties of basesheets were measured, the number of plies used varied depending on the intended end use. For example, if the basesheet was intended to be used for 2-ply product, two plies of basesheet were combined and tested.

Wet CD Tensile

Wet tensile strength measurements are measured in the same manner as described for dry tensile above, but after the center portion of the previously conditioned sample strip has been saturated with distilled water immediately prior to loading the specimen into the tensile test equipment. Sample wetting is performed by first laying a single test strip onto a piece of blotter paper (Fiber Mark, Reliance Basis 120). A pad is then used to wet the sample strip prior to testing. The pad is a green, Scotch-Brite brand (3M) general purpose commercial scrubbing pad. To prepare the pad for testing, a full-size pad is cut approximately 2.5 inches long by 4 inches wide. A piece of masking tape is wrapped around one of the 4 inch long edges. The taped side then becomes the "top" edge of the wetting pad. To wet a tensile strip, the tester holds the top edge of the pad and dips the bottom edge in approximately 0.25 inches of distilled water located in a wetting pan. After the end of the pad has been saturated with water, the pad is then taken from the wetting pan and the excess water is removed from the pad by lightly tapping the wet edge three times across a wire mesh screen. The wet edge of the pad is then gently placed across the sample, parallel to the width of the sample, in the approximate center of the sample strip. The pad is held in place for approximately one second and then removed and placed back into the wetting pan. The wet sample is then immediately inserted into the tensile grips, so the wetted area is approximately centered between the upper and lower grips. The test strip should be centered both horizontally and vertically between the grips. (It should be noted that if any of the wetted portion comes into contact with the grip faces, the specimen must be discarded, and the jaws dried off before resuming testing.) The tensile test is then performed, and the peak load recorded as the wet CD tensile strength of this specimen. As with the dry CD tensile test, the characterization of a product is determined by the average of ten representative sample measurements.

Slosh Time

Slosh time is determined by the Slosh Box Test, which uses a bench-scaled apparatus to evaluate the breakup or dispersibility of flushable consumer products as they travel through the wastewater collection system. In this test, a clear plastic tank was loaded with a product and tap water or raw wastewater. The container was then moved up and down by a cam system at a specified rotational speed to simulate the movement of wastewater in the collection system. The initial breakup point and the time for dispersion of the product into pieces measuring 1×1 inch (25×25 mm) were recorded in the laboratory notebook. This 1×1 inch (25×25 mm) size is a parameter that is used because it reduces the potential of product recognition. The various components of the product were then screened and weighed to determine the rate and level of disintegration.

The slosh box water transport simulator consisted of a transparent plastic tank that was mounted on an oscillating platform with speed and holding time controller. The angle of incline produced by the cam system produces a water motion equivalent to 60 cm/s (2 ft/s), which is the minimum design standard for wastewater flow rate in an enclosed collection system. The rate of oscillation was controlled mechanically by the rotation of a cam and level system and was measured periodically throughout the test. This cycle mimics the normal back- and forth movement of wastewater as it flows through sewer pipe.

Room temperature tap water was placed in the plastic container/tank. The timer was set for six hours (or longer) and cycle speed is set for 26 rpm. The pre-weighed product was placed in the tank and observed as it underwent the agitation period. The time to first breakup and full dispersion were recorded in the laboratory notebook.

The test was terminated when the product reached a dispersion point of no piece larger than 1×1 inch (25×25 mm) square in size. At this point, the clear plastic tank was removed from the oscillating platform. The entire contents of the plastic tank were then poured through a nest of screens arranged from top to bottom in the following order: 25.40 mm, 12.70 mm, 6.35 mm, 3.18 mm, 1.59 mm (diameter opening). With a showerhead spray nozzle held approximately 10 to 15 cm (4 to 6 in) above the sieve, the material was gently rinsed through the nested screens for two minutes at a flow rate of 4 L/min (1 gal/min) being careful not to force passage of the retained material through the next smaller screen. After two minutes of rinsing, the top screen was removed and the rinsing continued for the next smaller screen, still nested, for two additional minutes. After rinsing was complete, the retained material was removed from each of the screens using forceps. The contents were transferred from each screen to a separate, labeled aluminum weigh pan. The pan was placed in a drying oven overnight at 103±3° C. The dried samples were allowed to cool down in a desiccator. After all the samples were dry, the materials from each of the retained fractions were weighed and the percentage of disintegration based on the initial starting weight of the test material were calculated.

EXAMPLES

Basesheets were made using a through-air dried papermaking process commonly referred to as "uncreped through-air dried" ("UCTAD") and generally described in U.S. Pat. No. 5,607,551, the contents of which are incorporated herein in a manner consistent with the present disclosure. Basesheets with a target bone dry basis weight of about 25 grams per square meter (gsm) were produced. The base sheets were then converted into embossed two-ply tissue products.

Basesheets were prepared using a three-layered headbox to form a web having a first outer layer, also referred to as the fabric or fabric contacting layer, a middle layer, and a second outer layer, also referred to the air contacting or air layer. Various wood pulp fibers including, southern softwood kraft pulp (SSWK), *eucalyptus* hardwood kraft pulp (EHWK) and northern softwood kraft pulp (NSWK), were used to form the various furnish layers as detailed in Table 3, below. In certain instances a debonder was added to the fabric contacting layer and/or a dry strength resin was added to the middle layer as detailed in Table 3, below.

TABLE 3

| Sample | First Outer Layer (wt %) | Middle Layer (wt %) | Second Outer Layer (wt %) | Chemical Add-On (kg/MT) |
|---|---|---|---|---|
| Inventive 1 | EHWK (30%) | NSWK (40%) | EHWK (30%) | ProSoft ® TQ-1003 (1.5) |
|  |  |  |  | FennoBond ® 3300 (0.5) |
| Inventive 2 | SSWK | SSWK | SSWK | ProSoft ® TQ-1003 (1.5) |
| Inventive 3 | EHWK (30%) | NSWK (40%) | EHWK (30%) | ProSoft ® TQ-1003 (1.5) |
|  |  |  |  | FennoBond ® 3300 (0.5) |

Each furnish was diluted to approximately 0.2 percent consistency and delivered to a layered headbox and deposited on a Voith Fabrics TissueForm V forming fabric (commercially available from Voith Fabrics, Appleton, WI). The wet web was vacuum dewatered to approximately 25 percent consistency and then subjected to rush transfer when transferred to the transfer fabric. The transfer fabric was the fabric described as "Fred" in U.S. Pat. No. 7,611,607 (commercially available from Voith Fabrics, Appleton, WI). The rush transfer rate was 28 percent. The web was then transferred to a Tissue Max EX through-air drying fabric (commercially available from Voith Fabrics, Appleton, WI). The web was dried with a through-air-dryer resulting in dried tissue web.

The dried tissue web was fed to a gravure printing line, similar to that shown in FIG. 3, traveling at about 1,000 feet per minute where a latex-based binder was printed onto the surface of the sheet. The latex-based binder was Vinnapas® EP1133, commercially available from Wacker Polymers, LP (Allentown, PA) and consisted of 30 percent solids. The pH of the latex-based binder was adjusted using NaOH to a pH of approximately 6.0 and allowed to mix for approximately 5-30 minutes prior to use in the gravure printing operation. The viscosity of the latex-based binder was in range from 30-60 cps when measured at room temperature using a viscometer (Brookfield® Synchro-lectric viscometer Model RVT, Brookfield Engineering Laboratories Inc. Stoughton, MA) with a #1 spindle operating at 20 rpm.

The first side of the dried web was printed with the latex-based binder using direct rotogravure printing in a pattern as shown in FIG. 5. The pattern comprises three elongated hexagons having a length of about 0.02 inch (0.51 mm) and a width of about 0.006 inch (0.15 mm). After printing, the sheet was pressed against, and doctored off, a rotating drum having a surface temperature of approximately 126° C. to yield a print creped tissue web.

The print creped tissue web was subjected to further converting to produce a two-ply tissue product. Individual tissue webs were embossed and plied using an embossing-laminating device, such as those described in U.S. Pat. No. 3,867,225. The individual plies were arranged such that the surface printed with the latex-based binder formed the two outer surface of the two-ply tissue product.

After embossing and lamination Inventive Code 3 was treated with a softening composition. The contents of the softening composition are provided in Table 4, below.

TABLE 4

|  | Softening Composition |
|---|---|
| Silicone (wt %) | 2 |
| Glycerin (wt %) | 6 |

TABLE 4-continued

|  | Softening Composition |
|---|---|
| Nonionic Surfactant (wt %) | 5 |
| PEG-1,000 (wt %) | 7 |
| Water (wt %) | 80 |

The softening compositions were applied by offset gravure printing. The add-on levels where controlled by changing the gravure roll cell volume (measured as BCM—billion cubic microns per square inch), which was 6 BCM. The print creped tissue multi-ply web was wound onto a core and converted into a multi-ply rolled tissue product, which was subject to further physical testing as summarized in Tables 5 and 6, below.

TABLE 5

| Sample | Basis wt. (gsm) | Caliper (μm) | Sheet Bulk (cc/g) | GMT (g/3") | CD Tensile (g/3") | Wet CD Tensile (g/3") | Wet/Dry Ratio | Wet Burst (gf) | Slosh time (sec.) |
|---|---|---|---|---|---|---|---|---|---|
| Inventive 1 | 57.4 | 508 | 8.9 | 1631 | 1233 | 113 | 0.09 | 159 | 22 |
| Inventive 2 | 48.7 | 541 | 11.1 | 956 | 775 | 125 | 0.16 | 136 | 34 |
| Inventive 3 | 54.6 | 678 | 12.4 | 1178 | 942 | 145 | 0.15 | 172 | 39 |

TABLE 6

| Sample | GM Slope (kg) | GM TEA (g·cm/cm$^2$) | Dry Burst (gf) | GM Tear (gf) | Stiffness Index | TEA Index | Burst Index | Tear Index | Durability Index |
|---|---|---|---|---|---|---|---|---|---|
| Inventive 1 | 8.50 | 27.36 | 1607 | 23.24 | 5.2 | 1.68 | 9.85 | 1.42 | 12.96 |
| Inventive 2 | 4.91 | 14.54 | 951 | 15.80 | 5.1 | 1.52 | 9.94 | 1.65 | 13.12 |
| Inventive 3 | 5.07 | 18.95 | 1328 | 28.88 | 4.3 | 1.61 | 11.28 | 2.45 | 15.34 |

Embodiments

First embodiment: A creped, multi-ply tissue product comprising a first and a second tissue ply, the product having a geometric mean tensile strength (GMT) greater than about 700 g/3", a Durability Index of about 10.0 or greater and a Slosh time less than about 2 minutes.

Second embodiment: The product of the first embodiment having a Stiffness Index less than about 6.0.

Third embodiment: The product of embodiments 1 or 2 having a first outer surface and a non-crosslinked latex polymer disposed thereon.

Fourth embodiment: The product of any one of embodiments 1 through 3 having a first outer surface and a creping composition consisting essentially of a non-crosslinked vinyl acetate-ethylene polymer and optionally an anti-blocking agent disposed on the first outer surface. In certain embodiments the anti-blocking agent may comprise a polysaccharide or a surfactant.

Fifth embodiment: The product of any one of embodiments 1 through 4 having a GMT from about 700 to about 1,700 g/3".

Sixth embodiment: The product of any one of embodiments 1 through 5 having a Burst Index greater than about 8.0.

Seventh embodiment: The product of any one of embodiments 1 through 6 having a dry burst greater than about 1,000.

Eighth embodiment: The product of any one of embodiments 1 through 7 having a Stiffness Index from about 4.0 to about 6.0.

Ninth embodiment: The product of any one of embodiments 1 through 8 having a TEA Index greater than about 1.50.

Tenth embodiment: The product of any one of embodiments 1 through 9 wherein the first and the second creped tissue ply comprises a plurality of embossments.

Eleventh embodiment: The product of any one of embodiments 1 through 10 having a GM TEA greater than about 14.5 g·cm/cm$^2$.

Twelfth embodiment: The product of any one of embodiments 1-11 having a wet CD tensile greater than about 100 g/3".

Thirteenth embodiment: The product of any one of embodiments 1 through 12 having a Wet/Dry Ratio from about 0.10 to about 0.15.

Fourteenth embodiment: The product of any one of embodiments 1 through 13 comprising a first and a second outer surface and at least one softening composition selected from the group consisting of a polyhydroxy compound having a molecular weight of at least about 1,000 g/mol, a diamidoamine quaternary compound, an ester quaternary compound, an alkoxy alkyl quaternary compound, a benzyl quaternary compound, an alkyl quaternary compound, an imidazolinium quaternary compound, a polysiloxane, glycerin disposed on the first or the second outer surface.

Fifteenth embodiment: The product of any one of embodiments 1 through 14 having a basis weight from about 45 to about 60 grams per square meter (gsm) and a sheet bulk greater than about 8.0 cubic centimeters per gram (cc/g).

Sixteenth embodiment: The product of any one of embodiments 1 through 15 having a Slosh time from about 15 to about 45 seconds and a wet burst strength from about 150 to about 200 gf.

What is claimed is:

1. A method of manufacturing a rolled tissue product comprising the steps of:
   a. providing a first tissue web;
   b. providing a heated creping surface;
   c. applying a non-crosslinked vinyl acetate-ethylene polymer to the first tissue web;
   d. adhering the first tissue web to the heated creping surface;
   e. removing the adhered first tissue web from the heated creping surface to yield a creped tissue ply;
   f. plying two or more creped tissue plies together to form a multi-ply tissue product, wherein the multi-ply tissue product has a geometric mean tensile strength (GMT) greater than about 700 g/3", a Durability Index of about 10.0 or greater and a Slosh time less than about 2 minutes.

2. The method of claim 1 further comprising the step of applying a softening composition to the creped tissue ply or the multi-ply tissue product, wherein the softening composition is selected from the group consisting of a polyhydroxy compound having a molecular weight of at least about 1,000 g/mol, a diamidoamine quaternary compound, an ester quaternary compound, an alkoxy alkyl quaternary compound, a benzyl quaternary compound, an alkyl quaternary compound, an imidazolinium quaternary compounds, a polysiloxane and glycerin.

3. The method of claim 1 further comprising the step of applying an anti-blocking agent to the heated creping surface, wherein the anti-blocking agent is selected, from the group consisting of surfactants, silicones, waxes and polysaccharides.

4. The method of claim 1 further comprising the step of embossing the creped tissue ply.

5. The method of claim 1 further comprising the step of spirally winding the multi-ply tissue product around a core to yield a rolled tissue product.

6. The method of claim 1 wherein the first tissue web consists essentially of wood pulp fibers.

7. The method of claim 1 wherein the first tissue web has a basis weight ranging from about 10 to about 30 grams per square meter (gsm).

8. The method of claim 1 wherein the multi-ply tissue product has a GMT from about 700 to about 1,700 g/3".

9. The method of claim 1 wherein the multi-ply tissue product has a wet CD tensile from about 110 to about 160 g/3".

10. The method of claim 1 wherein the multi-ply tissue product has a Wet/Dry Ratio from about 0.10 to about 0.15.

11. The method of claim 1 wherein the multi-ply tissue product has a Durability Index of about 15.0 or greater.

12. The method of claim 1 wherein the multi-ply tissue product has a Stiffness Index from about 4.0 to about 6.0.

13. The method of claim 1 wherein the multi-ply tissue product has a Slosh time from about 15 to about 45 seconds and a wet burst strength from about 150 to about 200 gf.

14. The method of claim 1 wherein the step of removing the adhered first tissue web from the heated creping surface to yield a creped tissue ply is carried out by a contacting the adhered tissue web with a creping blade.

15. The method of claim 1 wherein the non-crosslinked vinyl acetate-ethylene polymer is applied to the first tissue web in a pattern.

16. The method of claim 15 wherein the pattern is a continuous pattern.

17. The method of claim 16 wherein the density of discrete dots ranges from about 25 to about 35 dots per square inch (25.4 $mm^2$) of tissue web surface area.

18. The method of claim 15 wherein the pattern comprises a plurality of discrete dots.

19. The method of claim 15 wherein the pattern is a continuous reticulated pattern.

20. The method of claim 1 wherein the non-crosslinked vinyl acetate-ethylene polymer is applied to the first tissue web by gravure printing, spraying, flexographic printing or ink jet printing.

* * * * *